United States Patent
Abe

(10) Patent No.: US 8,376,944 B2
(45) Date of Patent: Feb. 19, 2013

(54) CALORIC CONSUMPTION MEASURING DEVICE, CALORIC CONSUMPTION MEASURING METHOD, AND CALORIC CONSUMPTION MEASUREMENT PREPARATION PROCESSING METHOD

(75) Inventor: Ryuji Abe, Osaka (JP)

(73) Assignee: Shimano Inc., Osaka (JP)

( * ) Notice: Subject to any disclaimer, the term of this patent is extended or adjusted under 35 U.S.C. 154(b) by 1129 days.

(21) Appl. No.: 12/271,984

(22) Filed: Nov. 17, 2008

(65) Prior Publication Data

US 2009/0221883 A1 Sep. 3, 2009

(30) Foreign Application Priority Data

Feb. 28, 2008 (JP) ................. 2008-048233

(51) Int. Cl.
*A61B 5/00* (2006.01)
*A61B 5/02* (2006.01)
*A61B 5/04* (2006.01)
*A61B 5/08* (2006.01)

(52) U.S. Cl. ........ 600/301; 600/508; 600/509; 600/520; 600/530

(58) Field of Classification Search .................. None
See application file for complete search history.

(56) References Cited

U.S. PATENT DOCUMENTS

| | | | |
|---|---|---|---|
| 6,030,342 A | 2/2000 | Amano et al. | |
| 6,605,044 B2 | 8/2003 | Bimbaum | |
| 7,108,659 B2 * | 9/2006 | Ross et al. | 600/529 |
| 7,643,873 B2 * | 1/2010 | Chan | 600/520 |
| 2003/0208133 A1 * | 11/2003 | Mault | 600/532 |
| 2005/0177051 A1 * | 8/2005 | Almen | 600/509 |
| 2007/0049461 A1 | 3/2007 | Kim et al. | |
| 2008/0139952 A1 * | 6/2008 | Kuroda et al. | 600/508 |

FOREIGN PATENT DOCUMENTS

| | | |
|---|---|---|
| CN | 1198086 A | 11/1998 |
| JP | 05-212136 A | 8/1993 |
| JP | 09-56705 A | 3/1997 |
| JP | 2001-321370 A | 11/2001 |
| JP | 2002-336219 A | 11/2002 |
| JP | 2003-265448 A | 9/2003 |
| TW | 263488 | 10/2006 |

* cited by examiner

*Primary Examiner* — Sam Yao
*Assistant Examiner* — Shirley Jian
(74) *Attorney, Agent, or Firm* — Global IP Counselors, LLP

(57) ABSTRACT

A caloric consumption measuring device measures a caloric consumption of a user during an activity. The caloric consumption measuring device includes a first personal data creating component, a second personal data creating component, a heart rate input component, and a caloric consumption calculating component. The first personal data creating component sets at least one personal physical condition of the user and creates first personal data based on the set personal physical condition. The second personal data creating component sets at least one environmental condition of the user and creates second personal data based on the environmental condition. The heart rate input component receives data indicative of a detected heart rate. The caloric consumption calculating component calculates the caloric consumption based on the detected heart rate that was received and the first and second personal data created by the first and second personal data creating components.

5 Claims, 7 Drawing Sheets

|  | BASAL METABOLISM REFERENCE VALUE (kcal/m²/h) | |
| --- | --- | --- |
| YEAR (AGE) | MALE | FEMALE |
| 6 | 52.9 | 49.5 |
| 7 | 51.1 | 47.5 |
| 8 | 49.3 | 46.2 |
| 9 | 47.5 | 44.8 |
| 10 | 46.2 | 44.1 |
| 11 | 45.3 | 43.1 |
| 12 | 44.5 | 42.2 |
| 13 | 43.5 | 41.2 |
| 14 | 42.6 | 39.8 |
| 15 | 41.7 | 38.1 |
| 16 | 41.0 | 36.9 |
| 17 | 40.3 | 36.0 |
| 18 | 39.6 | 35.6 |
| 19 | 38.8 | 35.1 |
| 20 – 29 | 37.5 | 34.3 |
| 30 – 39 | 36.5 | 33.2 |
| 40 – 49 | 35.6 | 32.5 |
| 50 – 59 | 34.5 | 32.0 |
| 60 – 64 | 34.0 | 31.6 |
| 65 – 69 | 33.3 | 31.4 |
| 70 – 74 | 32.6 | 31.1 |
| 75 – 79 | 31.9 | 30.9 |
| 80 – | 30.7 | 30.7 |

*FIG. 6*

CALORIC CONSUMPTION MEASURING DEVICE, CALORIC CONSUMPTION MEASURING METHOD, AND CALORIC CONSUMPTION MEASUREMENT PREPARATION PROCESSING METHOD

CROSS-REFERENCE TO RELATED APPLICATIONS

This application claims priority under 35 U.S.C. §119 to Japanese Patent Application No. 2008-048233, filed on Feb. 28, 2008. The entire disclosure of Japanese Patent Application No. 2008-048233 is hereby incorporated herein by reference.

BACKGROUND OF THE INVENTION

1. Field of the Invention

This invention generally relates to an apparatus and method for measuring caloric consumption. In particular, the invention relates to a caloric consumption measuring device and caloric consumption measuring method configured to measure a caloric consumption of a user based on a heart rate of the user detected while the user is performing an activity.

2. Background Information

A known apparatus exists which measures a caloric consumption of a user during exercise using a correlation between a heart rate and an oxygen intake quantity (e.g., Japanese Laid-Open Patent Publication No. 9-56705). This known caloric consumption measuring device has a correlation table that expresses a pre-calculated correlation line in terms of the heart rate and the oxygen intake quantity. The heart rate and an acceleration are obtained from an output of a heart rate sensor and used to determine an exercise intensity, and the oxygen intake quantity is calculated using the correlation table and the exercise intensity. Since an oxygen intake quantity of 3.5 ml/kg/min corresponds to a caloric consumption of 1 kcal/min, the caloric consumption during exercise can be calculated if the oxygen intake quantity and the amount of time exercised are known.

The correlation table is contrived such that the slope of the heart rate versus oxygen intake quantity correlation line is changed depending on whether the exercise load is high or low, thus enabling the caloric consumption to be measured under various exercise loads. However, the caloric consumption measuring device does not take into account such personal differences as the age, sex, weight, and physical strength of the user and it is possible for an error to be incurred due to such differences.

Meanwhile, a known caloric consumption measuring device exists which takes into account personal differences (e.g., Japanese Laid-Open Patent Publication No. 2002-336216). This known caloric consumption measuring device is configured to measure a reference heart rate at a normal activity state for which the energy metabolic rate is known and calculate a reference caloric consumption for the normal activity state based on the known energy metabolic rate and a coefficient determined based on the age, weight, and sex of the user. A regression equation is then found for the calculated reference caloric consumption and the reference heart rate, and a caloric consumption corresponding to a heart rate occurring during exercise is calculated using the obtained regression equation. There are also cases in which two regression equations, one corresponding to an exercising state and one corresponding to a resting state, are used to calculate a caloric consumption.

The caloric consumption measuring device described above calculates the caloric consumption using a regression equation obtained based on actual exercise and enables the caloric consumption to be calculated in accordance with physical strength differences and other personal physical condition differences that exist among users. However, this approach incurs the disadvantage that the calculation of the regression equation is limited to an exercise (normal activity) for which the energy metabolic rate is known. Additionally, with this approach, in order to calculate the regression equation, the exercise for which the energy metabolic rate is known must actually be performed in order to obtain the reference heart rate and the reference caloric consumption. Thus, when the user will perform various types of exercise, a reference heart rate and a reference caloric consumption must be found for each exercise and the measurement of caloric consumption becomes complex.

SUMMARY OF THE INVENTION

One object of the invention is to make it possible to simply and accurately measure caloric consumption while taking into account personal differences.

In accordance with a first aspect, a caloric consumption measuring device is provided that measures a caloric consumption of a user during an activity. The caloric consumption measuring device includes a first personal data creating component, a second personal data creating component, a heart rate input component, and a caloric consumption calculating component. The first personal data creating component sets at least one personal physical condition of the user and creates first personal data based on the personal physical condition that was set. The second personal data creating component sets at least one environmental condition of the user and creates second personal data based on the environmental condition that was set. The heart rate input component is configured to receive data indicative of a detected heart rate. The caloric consumption calculating component is configured to calculate the caloric consumption based on the detected heart rate that was received and the first and second personal data created by the first and second personal data creating components.

With this caloric consumption measuring device, the first personal data creating component sets at least one personal physical condition of the user before measuring the caloric consumption and first personal data is created based on the set personal physical condition. Meanwhile the second personal data creating component sets an environmental condition of the user and creates second personal data based on the environmental condition that was set. After the two types of personal data are created, a detected heart rate is accepted and a caloric consumption is calculated based on the detected heart rate and the first and second personal data. With this aspect, the caloric consumption can be calculated by merely setting first personal data based on a personal physical condition and second personal data based on an environmental condition in advance. As a result, the caloric consumption can be measured easily without the need to perform an activity and take data before measuring the caloric consumption. Additionally, the caloric consumption can be calculated in accordance with personal differences because it is calculated based on both first personal data and second personal data. As a result, the caloric consumption can be measured simply and accurately while taking into account personal differences.

The heart rate mentioned here is not limited to a heart rate measured in close proximity to the heart of the user; the heart rate can also be a pulse measured at an arm or other location.

In accordance with a second aspect, the caloric consumption measuring device of the first aspect is provided such that the second personal data creating component is configured to set whether or not the user exercises regularly as at least part of the environmental condition. With this aspect, since information indicating whether or not the user exercises regularly is set as an environmental condition, the caloric consumption can be calculated accurately by taking into account whether the user is a person who exercises regularly or a person who does not in addition to taking into account the aforementioned personal physical conditions.

In accordance with a third aspect, the caloric consumption measuring device of the second aspect is provided such that the first personal data creating component includes a resting oxygen intake quantity calculating section that calculates a resting oxygen intake quantity as at least part of the first personal data, and the second personal data creating component further includes a flex point setting section that sets a plurality of flex points as boundary heart rates between a resting metabolism and an active metabolism and that sets a plurality of heart rate regions as at least part of the second personal data in accordance with whether or not the user exercises regularly. Also the second personal data creating component further includes a coefficient setting section that sets energy consumption coefficients as at least part of the second personal data, with the energy consumption coefficients being set for each of the heart rate regions and for each case of regular exercise and no regular exercise. With this aspect, the caloric consumption can be calculated in accordance with a heart rate region that is divided in three or more stages because a plurality of flex points are set as boundary heart rates between a resting metabolism and an active metabolism. As a result, the caloric consumption (which increases exponentially with respect to the heart rate) can be calculated more accurately. Additionally, the accuracy of the calculation of the resting oxygen intake quantity increases because the resting oxygen intake quantity is calculated based on the set personal physical conditions.

In accordance with a fourth aspect, the caloric consumption measuring device of the third aspect is provided such that the second personal data creating component further includes a maximum oxygen intake quantity calculating section that calculates a maximum oxygen intake quantity as at least part of the second personal data in accordance with whether or not the user exercises regularly. Also, the caloric consumption calculating component further includes a heart rate determining section that determines which of the heart rate regions includes the detected heart rate, a heart rate preparation value calculating section that calculates a heart rate preparation value for the heart rate region determined to contain the detected heart rate, and a calculating section that calculates an oxygen intake quantity at the detected heart rate and calculates the caloric consumption using the maximum oxygen intake quantity, the resting oxygen intake quantity, the energy coefficients for the heart rate region determined to contain the detected heart rate and a heart rate region lying on a higher heart rate side of the heart rate region determined to contain the detected heart rate, and the heart rate preparation value. With this aspect, the accuracy with which the oxygen intake quantity (which is proportional to the caloric consumption) is calculated is improved because the oxygen intake quantity is calculated using a heart rate preparation value that indicates an exercise intensity.

In accordance with a fifth aspect, the caloric consumption measuring device of the fourth aspect is provided such that the second personal data creating component further includes an estimated maximum heart rate calculating section that calculates an estimated maximum heart rate as at least part of the second personal data in accordance with whether or not the user exercises regularly; and the heart rate preparation value calculating section is configured to calculate the heart rate preparation value using the estimated maximum heart rate and two high and low flex points of the heart rate region determined to contain the detected heart rate. With this aspect, the accuracy with which the heart rate preparation value is calculated is increased because the heart rate preparation value can be calculated in a manner that takes into account a situation in which the maximum heart rate of a person who exercises regularly is lower than the maximum heart rate of a person who does not exercise regularly.

In accordance with a sixth aspect, the caloric consumption measuring device of the first aspect is provided such that the caloric consumption measuring device further comprises a display component configured to display a caloric consumption calculated by the caloric consumption calculating component. With this aspect, a user can check the caloric consumption during an activity because the caloric consumption is displayed.

In accordance with a seventh aspect, a caloric consumption measuring method is configured to measure a caloric consumption of a user during an activity and comprises a preparation processing step and a caloric consumption calculating step. The preparation processing step includes inputting at least one personal physical condition of the user, creating first personal data based on the personal physical condition, inputting at least one environmental condition that is not a physical condition of the user, creating second personal data based on the environmental condition, and inputting data indicative of a detected heart rate of the user. The caloric consumption calculating step includes calculating a caloric consumption based on the detected heart rate and the first and second personal data created in the preparation processing step.

With this caloric consumption measuring method, such personal physical conditions as the age, sex, height, and weight of the user are set before measuring the caloric consumption, and such first personal data as a resting oxygen intake quantity is created based on the set personal physical conditions. Meanwhile second personal data is created based on the inputted environmental condition. After the two types of personal data are created, a detected heart rate is inputted and a caloric consumption is calculated based on the detected heart rate and the first and second personal data. With this aspect, the caloric consumption can be calculated by merely setting first personal data based on personal physical conditions and second personal data based on an environmental condition in advance. As a result, the caloric consumption can be measured easily without the need to perform an activity and take data before measuring the caloric consumption. Additionally, the caloric consumption can be calculated in accordance with personal differences because it is calculated based on both first personal data and second personal data. As a result, the caloric consumption can be measured simply and accurately while taking into account personal differences.

In accordance with an eighth aspect, the caloric consumption measuring method of the seventh aspect is provided such that the inputting of the environmental condition includes inputting whether or not the user exercises regularly as the environmental condition. With this aspect, since information indicating whether or not the user exercises regularly is set as an environmental condition, the caloric consumption can be calculated accurately by taking into account whether the user is a person who exercises regularly or a person who does not in addition to taking into account the personal physical conditions.

In accordance with a ninth aspect, the caloric consumption measuring method of the eighth aspect is provided such that the creating of the first personal data includes calculating a resting oxygen intake quantity as at least part of the first personal data, and the creating of the second personal data includes setting a plurality of flex points as boundary heart rates between a resting metabolism and an exercising metabolism, setting a plurality of heart rate regions as at least part of the second personal data in accordance with whether or not the user exercises regularly, and setting energy consumption coefficients as at least part of the second personal data for calculating an energy consumption, being set for each of the heart rate regions and each case of regular exercise and no regular exercise. With this aspect, the caloric consumption can be calculated in accordance with a heart rate region that is divided in three or more stages because a plurality of flex points are set as boundary heart rates between a resting metabolism and an active metabolism. As a result, the caloric consumption (which increases exponentially with respect to the heart rate) can be calculated more accurately. Additionally, the accuracy of the calculation of the resting oxygen intake quantity increases because the resting oxygen intake quantity is calculated based on the set personal physical conditions.

In accordance with a tenth aspect, the caloric consumption measuring method of the ninth aspect is provided such that the creating of the second personal data includes calculating a maximum oxygen intake quantity as at least part of the second personal data in accordance with whether or not the user exercises regularly; and the calculating of the caloric consumption includes determining which of the heart rate regions contains the detected heart rate, calculating a heart rate preparation value for the heart rate region determined to contain the detected heart rate, calculating an oxygen intake quantity at the detected heart rate, and calculating the caloric consumption using the maximum oxygen intake quantity, the resting oxygen intake quantity, the energy coefficients for the heart rate region determined to contain the detected heart rate and for a heart rate region lying on a higher heart rate side of the heart rate region determined to contain the detected heart rate, and the heart rate preparation value. With this aspect, the accuracy with which the oxygen intake quantity (which is proportional to the caloric consumption) is calculated is improved because the oxygen intake quantity is calculated using a heart rate preparation value that indicates an exercise intensity.

In accordance with an eleventh aspect, the caloric consumption measuring method of the tenth aspect is provided such that the creating of the second personal data further includes calculating an estimated maximum heart rate as at least part of the second personal data in accordance with whether or not the user exercises regularly, and calculating the heart rate preparation value using the estimated maximum heart rate and two high and low flex points of the heart rate region determined to contain the detected heart rate. With this aspect, the accuracy with which the heart rate preparation value is calculated is increased because the heart rate preparation value is calculated in a manner that takes into account a situation in which the maximum heart rate of a person who exercises regularly is lower than the maximum heart rate of a person who does not exercise regularly.

In accordance with a twelfth aspect, a method of executing a preparation processing is configured to measure a caloric consumption of a user during an activity based on a detected heart rate of the user and comprises inputting at least one personal physical condition of the user, creating first personal data based on the personal physical condition, inputting at least one environmental condition that is not a physical condition of the user, and creating second personal data based on the environmental condition.

With this preparation processing execution method, such personal physical conditions as the age, sex, height, and weight of the user are set in the first setting step before measuring the caloric consumption and such first personal data as a resting oxygen intake quantity is created based on the set personal physical condition. Meanwhile the second personal data is created based on the set environmental condition. As a result, since the personal data can be set in advance in accordance with personal differences, the caloric consumption can be calculated easily in accordance with personal differences.

In accordance with a thirteenth aspect, the caloric consumption measuring method of the twelfth aspect is provided such that the inputting of the environmental condition includes inputting whether or not the user exercises regularly as the environmental condition. With this aspect, since information indicating whether or not the user exercises regularly is set as an environmental condition, the first and second personal data can be created accurately by taking into account whether the user is a person who exercises regularly or a person who does not, in addition to taking into account the personal physical conditions.

Accordingly, the caloric consumption can be calculated by merely setting first personal data based on personal physical conditions and second personal data based on an environmental condition in advance. As a result, the caloric consumption can be measured easily without the need to perform an activity and take data before measuring the caloric consumption. Additionally, the caloric consumption can be calculated in accordance with personal differences because it is calculated based on both first personal data and second personal data. As a result, the caloric consumption can be measured simply and accurately while taking into account personal differences.

These and other objects, features, aspects and advantages of the invention will become apparent to those skilled in the art from the following detailed description, which, taken in conjunction with the annexed drawings, discloses a preferred embodiment of the invention.

BRIEF DESCRIPTION OF THE DRAWINGS

Referring now to the attached drawings which form a part of this original disclosure:

FIG. 6 is a table showing an example of the basal metabolism reference values used depending on the age and sex of the user.

DETAILED DESCRIPTION OF THE PREFERRED EMBODIMENT

Selected embodiments of the invention will now be explained with reference to the drawings. It will be apparent to those skilled in the art from this disclosure that the following descriptions of the embodiments of the invention are provided for illustration only and not for the purpose of limiting the invention as defined by the appended claims and their equivalents.

Figure 1:
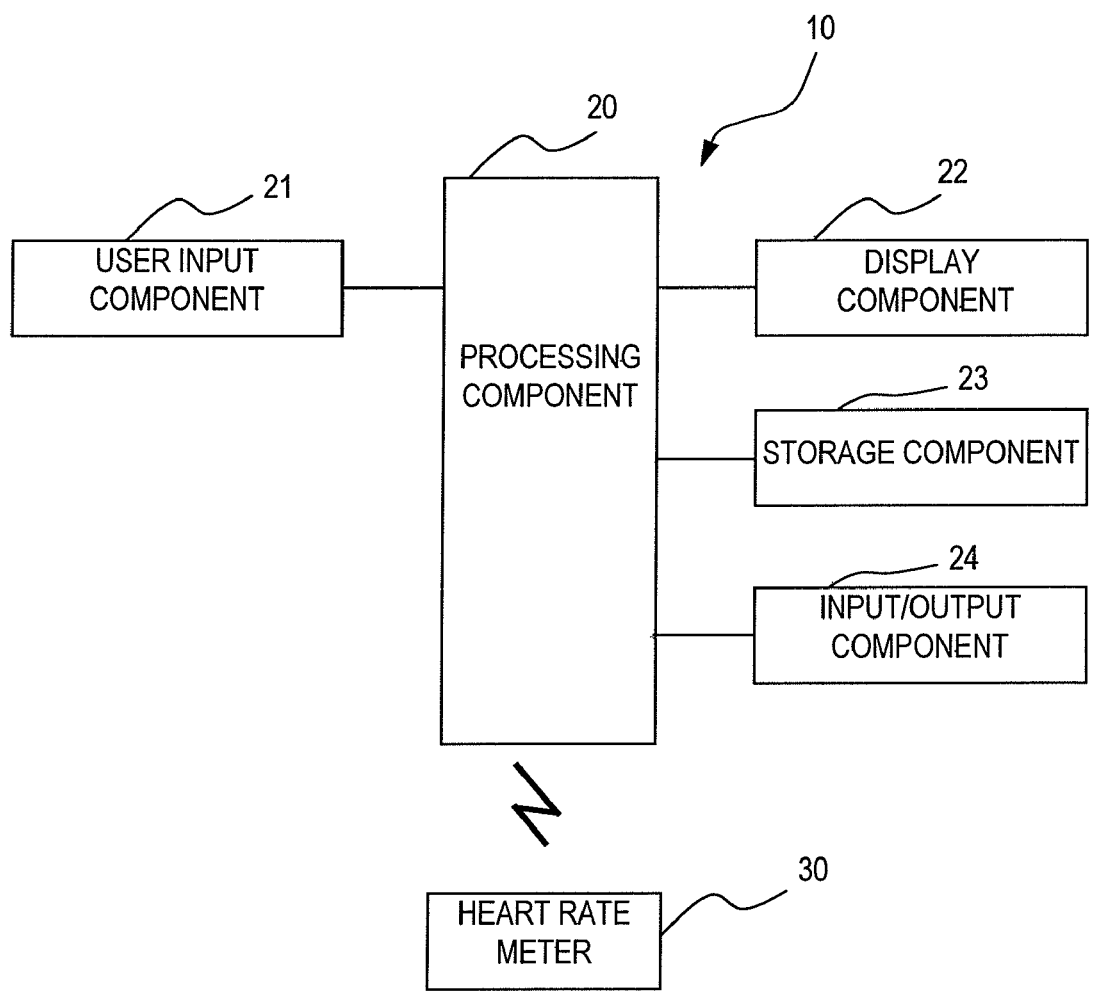
FIG. 1 is a block diagram showing the hardware configuration of a caloric consumption measuring device in accordance with an embodiment.

FIG. 1 shows a caloric consumption measuring device 10 in accordance with one embodiment. The caloric consumption measuring device 10 is configured to be attached to, for example, clothing or a handlebar of a bicycle. The caloric consumption measuring device 10 has a processing component 20 configured to calculate a caloric amount consumed during activity based on a heart rate. Connected to the processing component 20 are a user input component 21 and a display component 22 that displays a measured caloric amount. Also connected are, for example, a storage component 23 that includes a non-volatile memory and an input/output component 24 for other inputs and outputs.

The processing component 20 comprises a microprocessor including a RAM, a ROM and an input/output interface. The processing component 20 preferably communicates wirelessly with a heart rate meter 30 that detects a heart rate. The communication is preferably conducted using an existing standard that enables the processing component 20 and the heart rate meter 30 to identify each other. The heart rate meter 30 is configured such that it can be fastened on a surface of a user near the user's heart using a band or the like and such that it can communicate wirelessly with the processing component 20 using the aforementioned communication standard.

The user input component 21 has a plurality of input keys used, for example, for entering user data (described later) during the preparation processing executed before measuring a heart rate. The display component 22 is, for example, a color or monochromatic liquid crystal display that serves to display the content of setting operations and numeric values that have been set during preparation processing of user data and to display a calculated caloric value every five seconds (for example) during measurement of caloric consumption.

The storage component 23 stores two types of data, i.e., first personal data and second personal data (explained later) of a user that are set in advance before measuring a heart rate. The storage component 23 also stores tables and other numeric values necessary for calculating caloric amounts. The other input/output component 24 is provided with a USB connector or other connector for executing data transactions with a computer.

Figure 2:
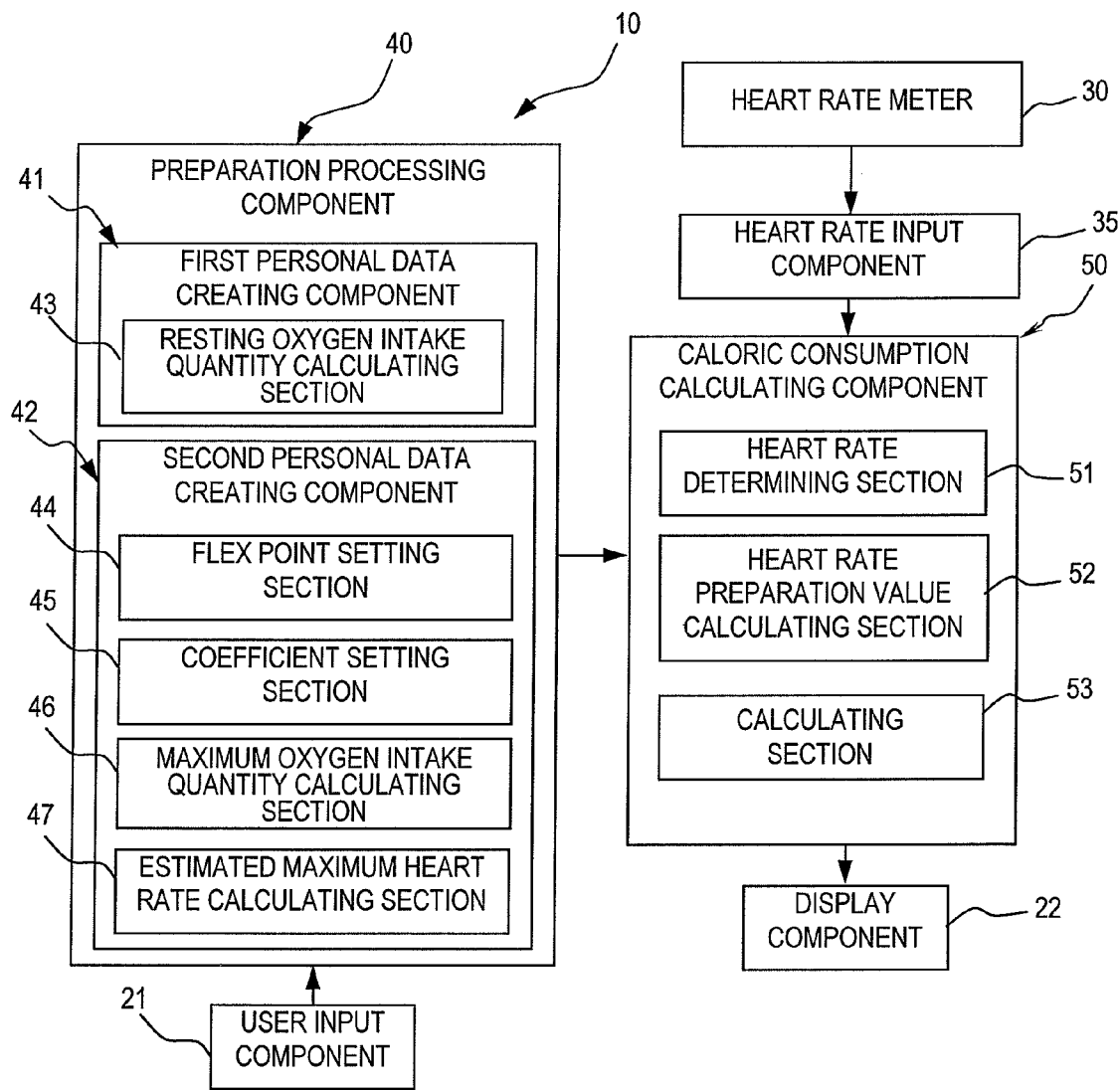
FIG. 2 is a block diagram showing the functional elements of the caloric consumption measuring device.

FIG. 2 is a block diagram of the functional elements of the caloric consumption measuring device 10. The caloric consumption measuring device 10 includes the following functional sections: a heart rate input component 35, a preparation processing component 40 and a caloric consumption calculating component 50. The heart rate input component 35 is configured to accept heart rate data HR from the heart rate meter 30. The preparation setting component 40 is configured to create first and second personal data based on information entered from the user input component 21. The caloric consumption calculating component 50 is configured to calculate a caloric consumption based on first and second personal data created by the preparation setting component 40 and output the caloric consumption to the display component 22.

The preparation setting component 40 has a first personal data creating component 41 and a second personal data creating component 42. The first personal data creating component 41 is configured to create first personal data. The second personal data creating component 42 is configured to create second personal data. The first personal data creating component 41 has a resting oxygen intake quantity calculating section 43. After personal physical conditions of the user (e.g., age, sex, height, and weight) are set, the resting oxygen intake quantity calculating section 43 creates a resting oxygen intake quantity ROI as first personal data based on the set personal physical conditions.

The second personal data creating component 42 sets whether or not the user exercises regularly as an environmental condition and creates second personal data based on the set condition of regular exercise or no regular exercise. The second personal data creating component 42 has a flex point setting section 44, a coefficient setting section 45, a maximum oxygen intake quantity calculating section 46 and an estimated maximum heart rate calculating section 47.

The flex point setting section 44 is configured to set a plurality of flex points (e.g., three flex points FP0 to FP2) as boundary heart rates between a resting metabolism and an active metabolism and set a plurality of heart rate regions (e.g., four heart rate regions BA0 to BA3) as at least part of the second personal data.

The coefficient setting section 45 is configured to set energy consumption coefficients ECC0 to ECC3 as at least part of the second personal data for calculating an energy consumption amount based on a heart rate. An energy consumption coefficient ECC0 to ECC3 is set for each of the heart rate regions and in accordance with whether or not the user exercises regularly.

The maximum oxygen intake quantity calculating section 46 is configured to set a maximum oxygen intake quantity MOI as at least part of the second personal data in accordance with whether or not the user exercises regularly. The estimated maximum heart rate calculating section 47 is configured to set an estimated maximum heart rate MHR as at least part of the second personal data in accordance with whether or not the user exercises regularly.

The caloric consumption calculating component 50 has a heart rate determining section 51, a heart rate preparation value calculating section 52 and a calculating section 53. The heart rate determining section 51 is configured to determine which of the heart rate regions BA0 to BA3 a detected heart rate lies within. The heart rate preparation value calculating section 52 is configured to calculate a heart rate preparation value HV1 to HV3 for the determined heart rate region. The calculating section 53 is configured to calculate a caloric consumption by calculating an oxygen intake quantity at the detected heart rate. The calculating section 53 is configured to calculate a caloric consumption using the maximum oxygen intake quantity MOI, the resting oxygen intake quantity ROI, the energy coefficients at the determined heart rate region and a heart rate region lying on a higher heart rate side of the determined heart rate region, and the heart rate preparation value.

The operation of the processing component 20 will now be explained briefly. The processing component 20 operates in accordance with a control program.

The processing component 20 first executes user data preparation processing for creating first and second personal data based on personal physical conditions of the user and whether or not the user exercises regularly. The processing component 20 then calculates a caloric consumption during activity based on the created first and second personal data. In this embodiment, the personal physical conditions are the height, weight, sex, and age of the user (the person whose heart rate will be measured) and the user is considered to exercise regularly if he or she exercises, for example, at least once per week on an on-going basis. The user enters this data during the user data preparation processing. Once the user data has been entered, the processing component 20 accepts the data and creates the first personal data and the second personal data, accepts a heart rate from the heart rate meter 30, and calculates a caloric consumption and displays a cumulative caloric consumption value on the display component 22, for example, once every five seconds. It is also acceptable to display a caloric consumption per unit of time separately.

The processing executed by the processing component 20 will now be explained in more detail with reference to the flowcharts shown in FIGS. 3 to 5.

Figure 3:
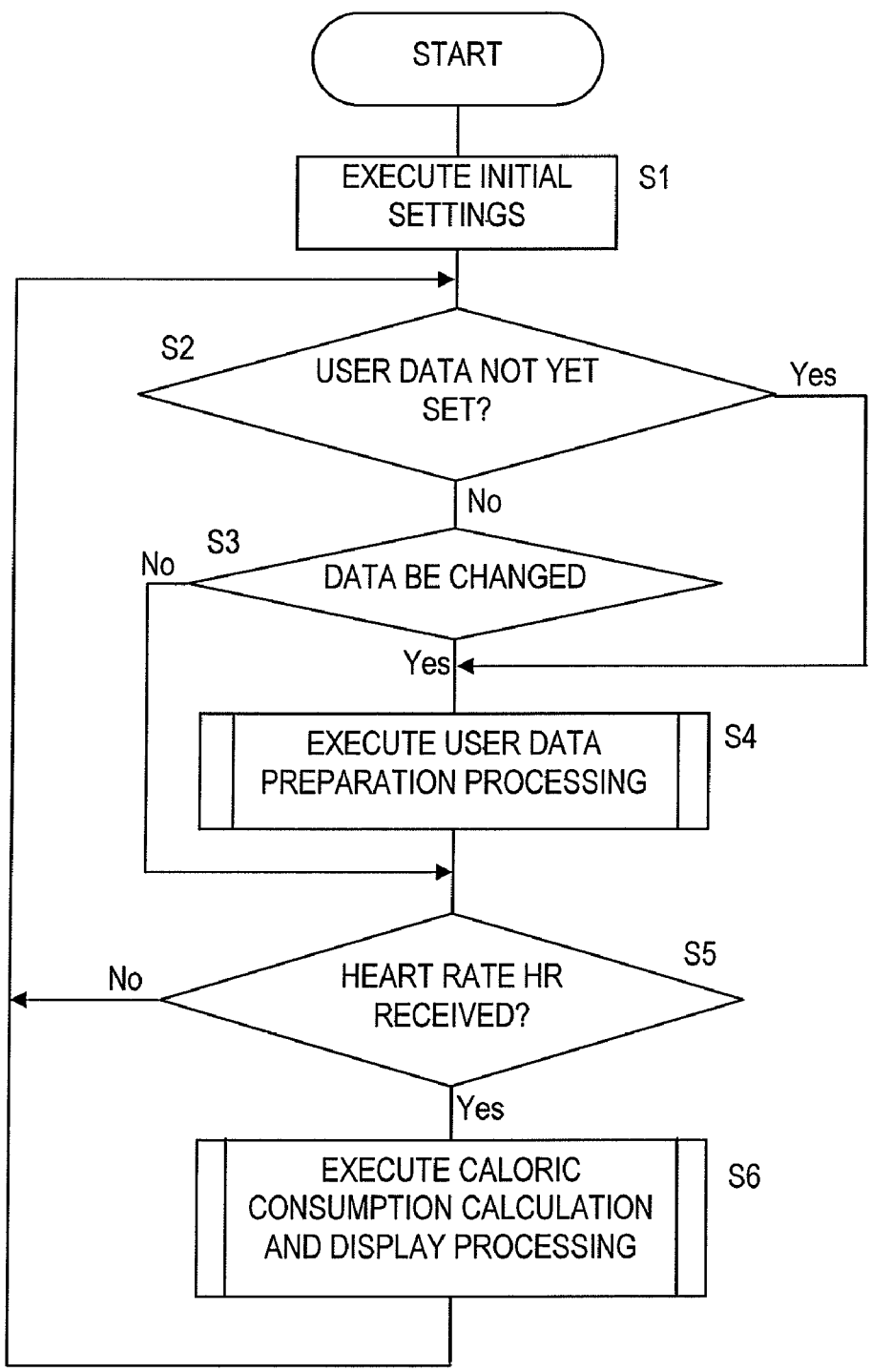
FIG. 3 is a flowchart showing the processing steps of a main routine of the caloric consumption measuring device.

When the power to the caloric consumption measuring device 10 is turned on, the processing component 20 executes initial settings in accordance with step S1 of FIG. 3. The initial settings involve receiving identification information from the heart rate meter 30 and executing settings for communication with the heart rate meter 30. If user data is already stored in the storage component 23 and the user data has been set, then the user data is acquired by the processing component 20.

In step S2, the processing component 20 determines if the user data has not yet been set. This determination is accomplished by checking the content stored in the storage component 23. If the user data has already been set, the processing component 20 proceeds to step S3. In step S3, the processing component 20 determines if the user has selected to change the user data settings. If the user has selected to change the settings by operating the user input component 21, then the result of step S3 is Yes. If the user has selected to change the settings, then the processing section proceeds to step S4. If the user has not selected to change the user settings, then the processing component 20 skips step S4 and proceeds to step S5. If user data has not yet been set, then the processing component 20 skips step S3 and proceeds to step S4.

Figure 4:
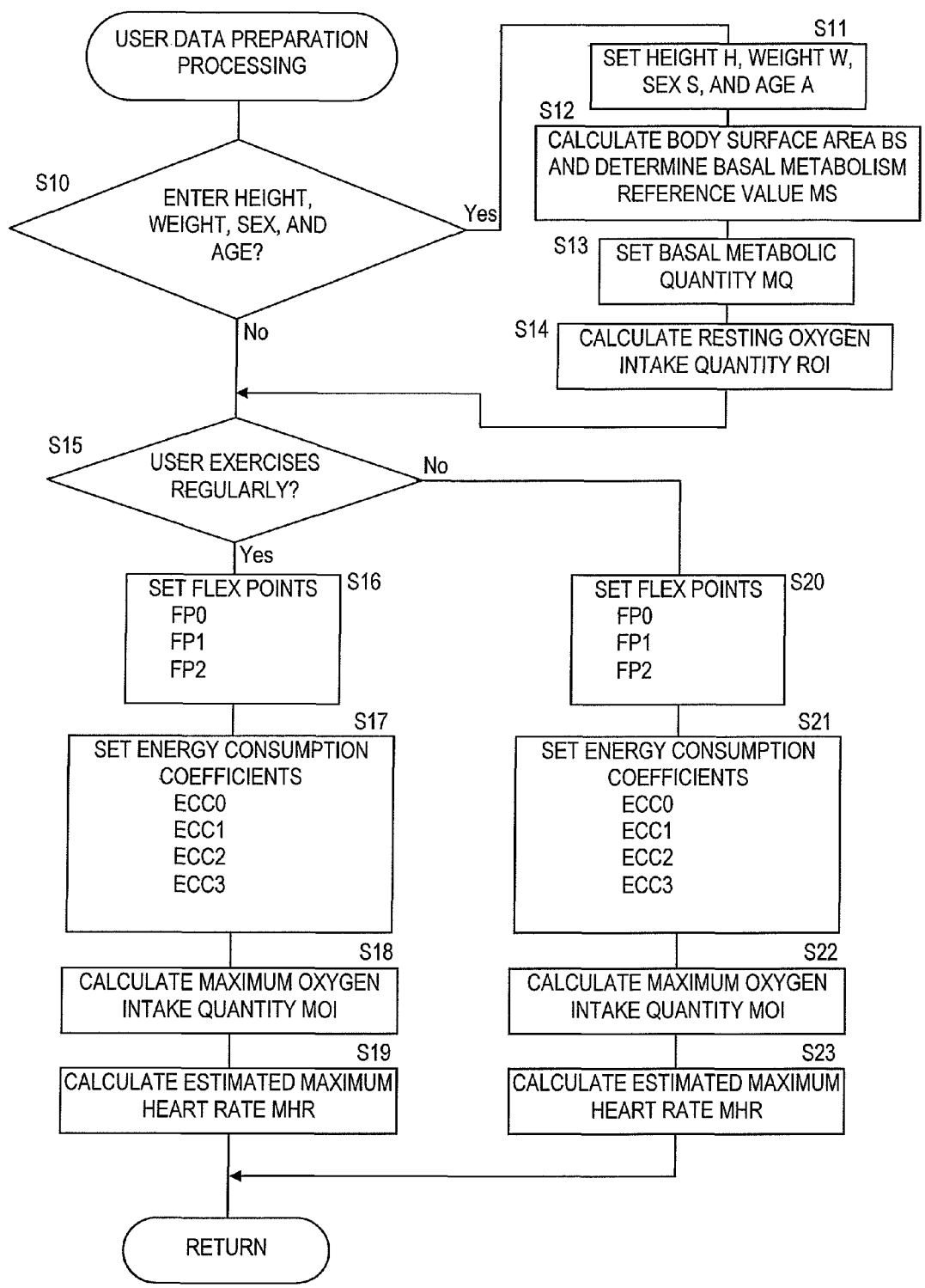
FIG. 4 is a flowchart showing the processing steps of a user data preparation processing routine of the caloric consumption measuring device.
Figure 5:
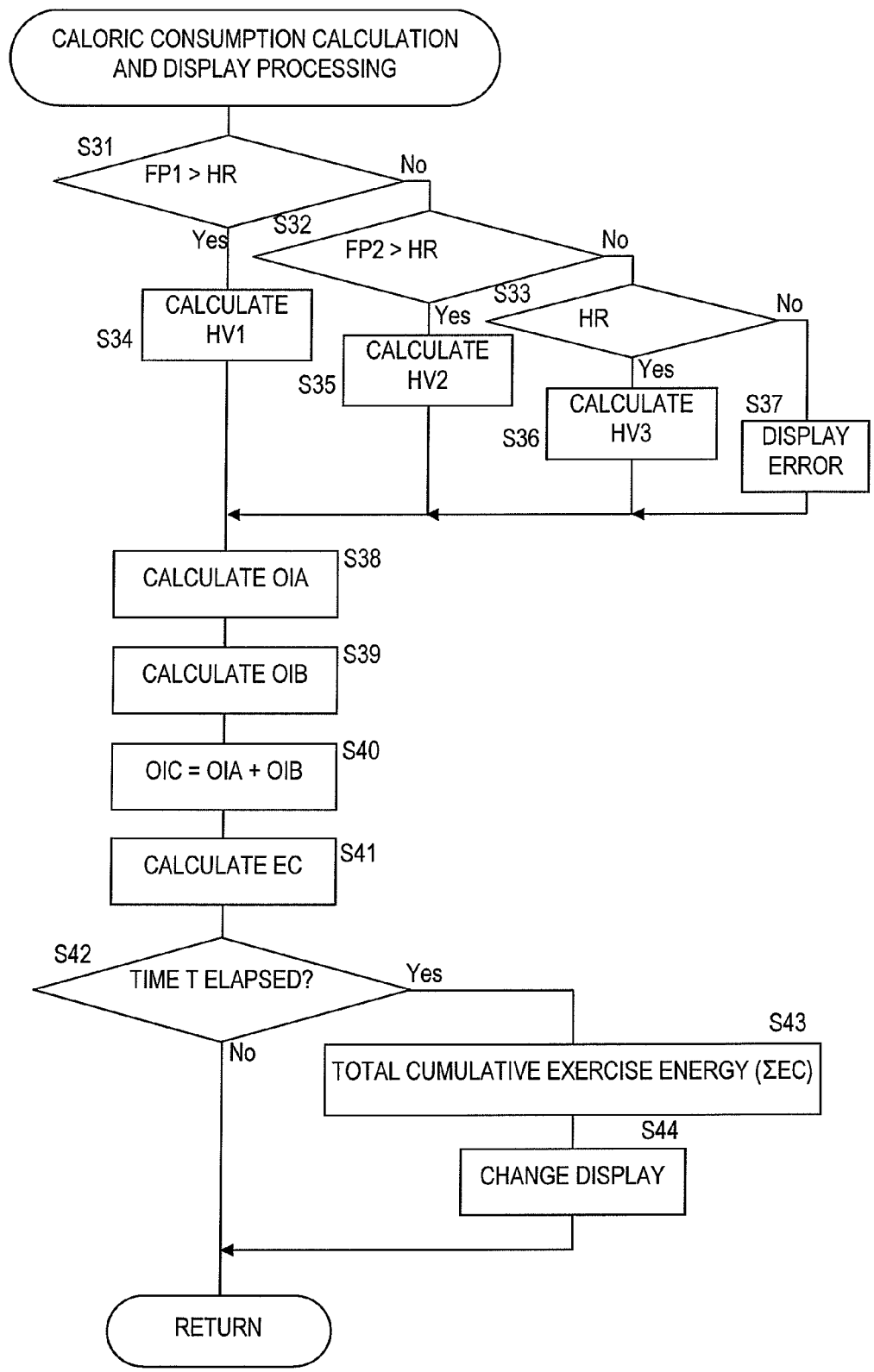
FIG. 5 is a flowchart showing the processing steps of a caloric consumption calculation and display routine of the caloric consumption measuring device.

In step S4, the processing component 20 executes a user data preparation processing shown in FIG. 4 before proceeding to step S5. Step S4 prepares the user data that will be used to measure the user's caloric consumption. In step S5, the processing component 20 determines if a heart rate HR datum has been received from the heart rate meter 30. If a heart rate HR datum has been received, then the processing component 20 accepts the datum and proceeds to step S6. In step S6, the processing component 20 executes the processing shown in FIG. 5 to calculate and display a caloric consumption and then returns to step S2.

The user data preparation processing executed in step S4 will now be explained with reference to FIG. 4. In step S10, the processing component 20 accepts personal physical condition data from the user. More specifically, the processing section accepts the height, weight, sex, and age of the user. More specifically, the user enters the personal physical condition data using the user input component 21, and the processing component 20 accepts the data. After accepting the personal physical condition data, the processing section proceeds to step S11. In step S11, the processing section sets the accepted height H, weight W, sex S, and age A into the storage component 23.

The personal physical condition data is used to calculate a body surface area BS (m$^2$) and determine a basal metabolism reference value MS (kcal/m$^2$/h), i.e., a metabolic quantity per unit surface area per unit time. More specifically, the body surface area BS is calculated using the equation (1) shown below.

$$\text{Body surface area BS}=((\text{weight W}^{0.444}\times\text{height H}^{0.663})\times 88.83)/10000 \quad (1)$$

The basal metabolism reference value MS is set based on the sex S and age A stored in the storage component 23 using the basal metabolism reference value determining table shown in FIG. 6. When step S12 is completed, the processing component 20 proceeds to step S13. In step S13, the processing component 20 calculates a basal metabolic quantity MQ (kcal/min). More specifically, the basal metabolic quantity MQ is calculated using the equation (2) shown below.

$$\text{Basal metabolic quantity MQ}=\text{basal metabolism reference value MS}\times\text{body surface area}/60 \quad (2)$$

In this embodiment, the value obtained by dividing the basal metabolic quantity MQ explained above by 12 (MQ/12) is actually used as the basal metabolic quantity because the caloric consumption is calculated every five minutes.

In step S14, the processing component 20 calculates a resting oxygen intake quantity ROI (ml/kg/min) by using the basal metabolic quantity MQ in the equation (3) shown below.

$$\text{Resting oxygen intake quantity ROI}=((\text{basal metabolic quantity MQ}/4.924)\times 1000)/\text{weight W} \quad (3)$$

In this embodiment, the value obtained by dividing the basal metabolic quantity MQ explained above by 12 (MQ/12) is actually used as the basal metabolic quantity because the caloric consumption is calculated every five minutes. When the processing described above is completed, the processing component 20 proceeds to step S15.

In step S15, the processing component 20 determines if the user exercises regularly nor not and accepts the related data. More specifically, the user enters data indicating whether or not the user exercises regularly using the user input component 21 and the processing component 20 accepts the data. If it determines that the user exercises regularly, then the processing component 20 proceeds to step S16. In step S16, the processing component 20 sets flex points FP appropriate for a case in which the user exercises regularly. The flex points FP are boundary heart rates between a resting metabolism and an active metabolism. In this embodiment, three flex points are set, i.e., first to third flex points FR0, FR1, and FR2. The first to third flex points FR0, FR1, and FR2 divide the heart rate region into four heart rate regions, i.e., first to fourth heart rate regions BA0, BA1, BA2, and BA3. It is acceptable to set the number of flex points to different numbers depending on the type of activity or other factor.

In this embodiment, the values of the flex points (heart rates expressed in bpm) FP0, FP1, and FP2 are set to 66, 85, and 115, respectively, if the user exercises regularly. In step S17, the processing component 20 sets a base energy consumption coefficient ECC for each of the heart rate regions corresponding to a case in which the user exercises regularly. Each of the basic energy consumption coefficients ECC is a coefficient indicating a ratio by which the active oxygen intake quantity increases with respect to the basal metabolic quantity MQ. In step S17, the processing component 20 sets the coefficient ECC0 of the first heart rate region BA0 to 1.7, the coefficient ECC1 of the second heart rate region BA1 to 1.7, the coefficient ECC2 of the third heart rate region BA2 to 3.5, and the coefficient ECC3 of the fourth heart rate region BA3 to 6.0.

In step S18, the processing component 20 calculates a maximum oxygen intake quantity MOI (ml/kg/min) for a case in which the user exercises regularly using the equation (4) shown below and proceeds to step S19.

$$\text{Maximum oxygen intake quantity MOI}=61.75-0.2747\times\text{age A} \quad (4)$$

In step S19, the processing component 20 calculates an estimated maximum heart rate MHR for a case in which the user exercises regularly using the equation (5) shown below. The processing component 20 then ends the user data preparation processing and returns to the main control routine.

$$\text{Estimated maximum heart rate MHR} = 208 - 0.7 \times \text{age A} \quad (5)$$

Conversely, if it determines that the user does not exercise regularly, then the processing component 20 proceeds from step S15 to step S20. In step S20, the processing component 20 sets three flex points FP0, FP1, and FP2 appropriate for a case in which the user does not exercise regularly. In this embodiment, the values of the flex points (heart rates expressed in bpm) FP0, FP1, and FP2 are set to 68, 87, and 120, respectively, if the user exercises regularly. These values are higher than for a case in which the user exercises regularly.

In step S21, the processing component 20 sets a basic energy consumption coefficient ECC for each of the heart rate regions corresponding to a case in which the user does not exercise regularly. In step S21, the processing component 20 sets the coefficient ECC0 of the first heart rate region BA0 to 1.6, the coefficient ECC1 of the second heart rate region BA1 to 1.6, the coefficient ECC2 of the third heart rate region BA2 to 3.3, and the coefficient ECC3 of the fourth heart rate region BA3 to 6.3. Thus, except for the fourth heart rate region BA3, the basic energy consumption coefficients ECC are set to lower values than for a case in which the user exercises regularly.

In step S22, the processing component 20 calculates a maximum oxygen intake quantity MOI (ml/kg/min) for a case in which the user does not exercise regularly using the equation (6) shown below and proceeds to step S23.

$$\text{Maximum oxygen intake quantity MOI} = 49.88 - 0.3019 \times \text{age A} \quad (6)$$

The maximum oxygen intake quantity MOI is calculated to be a smaller value than when the user exercises regularly.

In step S23, the processing component 20 calculates an estimated maximum heart rate MHR for a case in which the user does not exercise regularly using the equation (7) shown below. The processing component 20 then ends the user data preparation processing and returns to the main control routine.

$$\text{Estimated maximum heart rate MHR} = 220 - \text{age A} \quad (7)$$

Regarding the estimated maximum heart rate HR, the maximum value is higher than for a case in which the user exercises regularly, but the age A is not multiplied by 0.7. Consequently, the estimated maximum heart rate MHR is higher for users who do not exercise regularly up to age 40 and lower for users who do exercise regularly after age 40.

Figure 7:
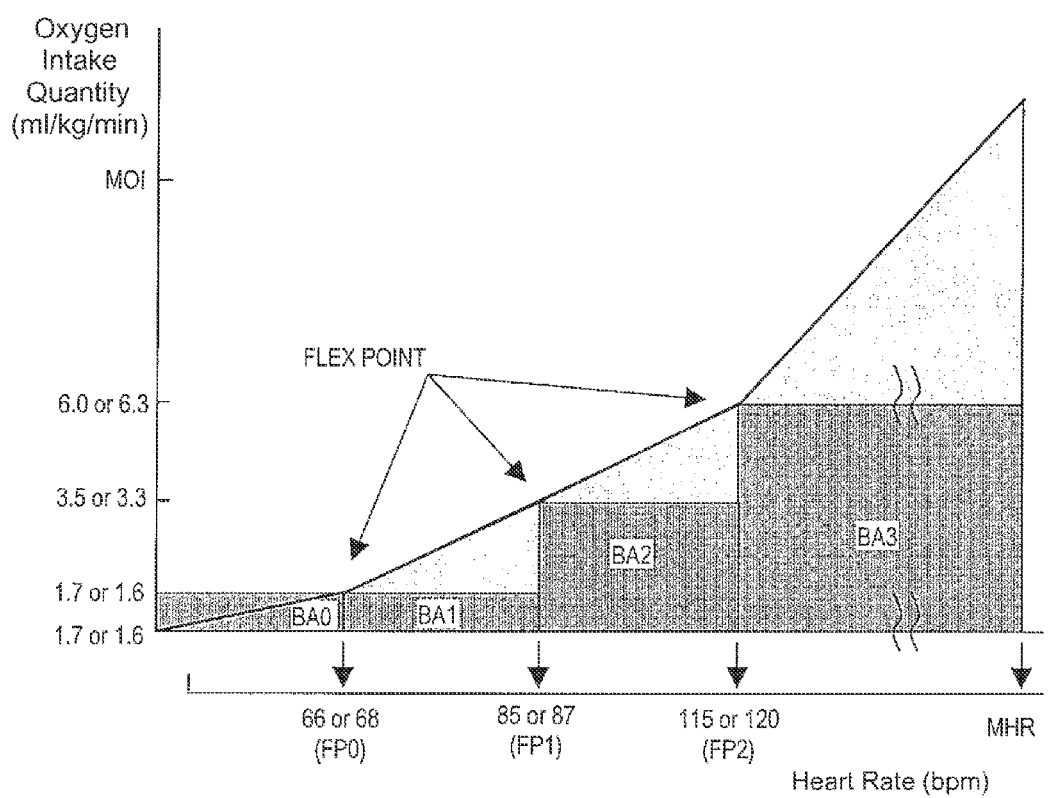
FIG. 7 is a graph showing the relationships among the heart rate, the oxygen intake quantity, the flex points, and the coefficients.

These relationships are illustrated with a graph in FIG. 7. In FIG. 7, the horizontal axis indicates the heart rate and the vertical axis indicates the oxygen intake quantity. The first to third flex points FP0 to FP2 corresponding to whether or not the user exercises regularly are shown on the horizontal axis along with numeric values and the graph is divided into first to fourth heart rate regions BA0 to BA3. Meanwhile, the numeric values of the coefficients ECC0 to ECC3 set for each of the heart rate regions BA0 to BA3 are shown on the vertical axis in accordance with whether or not the user exercises regularly. In the graph, each of the darkly shaded rectangular portions correspond to a second oxygen intake quantity OIB that spans from a basal metabolism of the particular heart rate region BA0, BA1, BA2 or BA3 to a basal oxygen intake quantity, and each of the triangular portions corresponds to a first oxygen intake quantity OIA that spans from the basal oxygen intake quantity to the current heart rate The oxygen intake quantity OIC during exercise can be calculated by adding the first and second oxygen intake quantities OIA and OIB together.

The caloric consumption calculation and display processing of FIG. 5 will now be explained. In steps S31 to S33, the processing section determines which of the first to fourth heart rate regions BA0 to BA3 the heart rate HR accepted in step S5 lies in by comparing it with the flex points FP0 to FP2 set during the preparation processing. If the heart rate HR is determined to be smaller than the first flex point FP0, i.e., if the heart rate HR lies in the first heart rate region BA0, then the first oxygen intake quantity OIA and a preparation value HV0 (discussed later) corresponding to the heart rate HR are set to 0.

If the detected heart rate HR is determined to lie in the second heart rate region BA1 (FP1>HR≧FP0), then the processing section proceeds from step S31 to S34. In step S34, the processing component 20 calculates a heart rate preparation value HV1 for the second heart rate region BA1 using the equation (8) shown below and proceeds to step S38.

$$HV1 = (\text{Current heart rate HR} - FP0)/(FP1 - FP0) \quad (8)$$

If the detected heart rate HR is determined to lie in the third heart rate region BA2 (FP2>HR≧FP1), then the processing section proceeds from step S31 to S35. In step S35, the processing component 20 calculates a heart rate preparation value HV2 for the third heart rate region BA2 using the equation (9) shown below and proceeds to step S38.

$$HV2 = (\text{Current heart rate HR} - FP1)/(FP2 - FP1) \quad (9)$$

If the detected heart rate HR is determined to lie in the fourth heart rate region BA3 (HR≧FP2), then the processing section proceeds from step S33 to S36. In step S36, the processing component 20 calculates a heart rate preparation value HV3 for the fourth heart rate region BA3 using the equation (10) shown below and proceeds to step S38.

$$HV3 = (\text{Current heart rate HR} - FP2)/(\text{estimated maximum heart rate MHR} - FP2) \quad (10)$$

In step S38, the processing component 20 calculates the first oxygen intake quantity OIA based on the obtained heart rate preparation value HV1, HV2, or HV3 and proceeds to step S39. The first oxygen intake quantity OIA indicates the oxygen intake quantity from the basal oxygen intake quantity to the current heart rate in the triangular portion of the graph shown in FIG. 7.

The first oxygen intake quantity OIA is calculated with the equation (11) shown below when the current heart rate is in the second or third heart rate region BA1 or BA2 and with the equation (12) shown below when the current heart rate is in the fourth heart rate region BA3.

$$\text{First oxygen intake quantity OIA} = ((\text{coefficient ECC2 or ECC3 of next higher heart rate region} \times \text{resting oxygen intake quantity ROI}) - (\text{coefficient ECC1 or ECC2 of current heart rate region} \times \text{resting oxygen intake quantity ROI})) \times \text{heart rate preparation value HV1 or HV2 for the current heart rate} \quad (11)$$

$$\text{First oxygen intake quantity OIA} = (\text{maximum oxygen intake quantity MOI} - (\text{coefficient ECC1 or ECC2 of current heart rate region} \times \text{resting oxygen intake quantity ROI})) \times \text{heart rate preparation value HV3 for the current heart rate} \quad (12)$$

In the equation (11) above, the resting oxygen intake quantity ROI is multiplied by the coefficient ECC1 or ECC2 of the next higher heart rate region, which enables the overall height (oxygen intake quantity) at the flex point FP1 or FP2 in FIG. 7 to be found. Then, by subtracting the product of the resting oxygen intake quantity and the coefficient corresponding to the current heart rate, the height of the triangular portion at the flex point FP1 or FP2 can be calculated. The height of the triangular portion at the current heart rate can then be calculated by multiplying the height at the flex point by the heart rate preparation value.

The equation (12) is used when the current heart rate is in the fourth heart rate region BA3. Since there is no next higher flex point, the maximum oxygen intake quantity MOI is used to find the overall height at that point in time. Then, the height of the triangular portion at the estimated maximum heart rate MHR can be found by multiplying the resting oxygen intake quantity by the coefficient corresponding to the current heart rate. The height of the triangular portion at the current heart rate can then be calculated by multiplying the height at the estimated maximum heart rate MHR by the heart rate preparation value.

In step S39, the processing component 20 calculates the second oxygen intake quantity OIB, i.e., the height of the rectangular portion of the basal oxygen intake quantity, using the equation (13) shown below and proceeds to step S40.

$$\text{Second oxygen intake quantity OIB} = \text{Coefficient ECC1, ECC2, or ECC3 of heart rate region BA1, BA2, or BA3 containing current heart rate} \times \text{resting oxygen intake quantity ROI} \quad (13)$$

When the current heart rate HR is determined to be smaller than the flex point FP0, i.e., in the first heart rate region BA0, the value of the second oxygen intake quantity OIB is fixed.

In step S40, the processing component 20 calculates an exercising oxygen intake quantity OIC by adding the first oxygen intake quantity OIA and the second oxygen intake quantity OIB together. In step S41, the processing component 20 calculates a caloric consumption EC based on the exercising oxygen intake quantity OIC. In step S42, the processing section waits for a display cycle setting time T (e.g., 5 seconds) to elapse. While waiting for the time T to elapse, the processing component 20 returns to the main routine from the caloric consumption calculation and display routine and proceeds from step S42 to step S43 when the time T has elapsed. In step S43, the caloric consumption calculated in step S41 is added into a summation to obtain a cumulative value. In step S44, the processing component 20 updates the calorie display to the new cumulative value and returns to the main routine.

This caloric consumption setting apparatus 10 can calculate a caloric consumption by merely setting first personal data and second personal data in advance, where the first personal data includes a resting oxygen intake quantity calculated based on such personal physical conditions as the height, weight, sex, and age of the user and the second personal data includes flex points FP0 to FP2, coefficients ECC1 to ECC3, an estimated maximum heart rate MHR, and a maximum oxygen intake quantity MOI determined in accordance with whether or not the user exercises regularly. As a result, it is not necessary to take measurements while performing an activity in advance, and the caloric consumption can be measured easily. Additionally, the caloric consumption can be calculated in accordance with personal differences because it is calculated based on both first personal data and second personal data. As a result, the caloric consumption can be measured simply and accurately while taking into account personal differences.

Additionally, the caloric consumption can be calculated in accordance with a heart rate region that is divided in three or more stages because a plurality of flex points FP are set as boundary heart rates between a resting metabolism and an active metabolism. As a result, the caloric consumption (which increases exponentially with respect to the heart rate) can be calculated more accurately.

Other Embodiments

Although in the embodiment three flex points are set, it is acceptable to set any number of flex points that is equal to or larger than 1.

The values presented in the embodiment for the flex points FP, the basic energy consumption coefficients, and the basal metabolism reference value are merely examples and do not limit the invention.

Although in the embodiment the height, weight, sex, and age of the user are used as personal physical condition data, the invention is not limited to these personal physical condition data. For example, such personal data as body fat can be used.

Although in the embodiment a user is determined to exercise regularly if the user exercises at least once per week, the invention is not limited to this definition of regular exercise. For example, the exercise regularity can be determined in terms of the number of times per month or the number of times per year.

Although in the embodiment information indicating whether or not the user exercises regularly is set as an environmental condition, information indicating such factors as the physical strength of the user, the physical condition of the user, the experience level of the user with respect to a particular exercise can be set as environmental conditions.

General Interpretation of Terms

In understanding the scope of the invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed.

While only selected embodiments have been chosen to illustrate the invention, it will be apparent to those skilled in the art from this disclosure that various changes and modifications can be made herein without departing from the scope of the invention as defined in the appended claims. Furthermore, the foregoing descriptions of the embodiments according to the invention are provided for illustration only, and not for the purpose of limiting the invention as defined by the appended claims and their equivalents.

What is claimed is:

1. A caloric consumption measuring device configured to measure a caloric consumption of a user during an activity, the caloric consumption measuring device comprising:

a first personal data creating component configured to set at least one personal physical condition of the user and create first personal data based on the personal physical condition that was set;

a second personal data creating component configured to set at least one environmental condition of the user and create second personal data based on the environmental condition that was set, the second personal data creating component being configured to set whether or not the user exercises regularly, a physical strength of the user, a physical condition of the user, or an experience level of the user with respect to a particular exercise as at least part of the environmental condition;

a heart rate input component configured to receive data indicative of a detected heart rate detected during the activity; and a caloric consumption calculating component configured to calculate the caloric consumption based on the detected heart rate that was received and the first and second personal data created by the first and second personal data creating components, the first personal data creating component including a resting oxygen intake quantity calculating section that calculates a resting oxygen intake quantity as at least part of the first personal data, the second personal data creating component further including a flex point setting section that sets a plurality of flex points as boundary heart rates between a resting metabolism and an active metabolism in accordance with the at least one environmental condition and that sets a plurality of heart rate regions as at least part of the second personal data in accordance with the at least one environmental condition, the flex points being defined by heart rate in relation to oxygen intake quantity, the second personal data creating component further including a coefficient setting section that sets energy consumption coefficients as at least part of the second personal data, with the energy consumption coefficients being set for each of the heart rate regions and for each case of environmental condition set by the second personal data creating component, the second personal data creating component further including a maximum oxygen intake quantity calculating section that calculates a maximum oxygen intake quantity as at least part of the second personal data in accordance with the at least one environmental condition set by the second personal data creating component, and the caloric consumption calculating component further including a heart rate determining section that determines which of the heart rate regions includes the detected heart rate, a heart rate preparation value calculating section that calculates a heart rate preparation value for the heart rate region determined to contain the detected heart rate, and a calculating section that calculates an oxygen intake quantity at the detected heart rate and calculates the caloric consumption using the maximum oxygen intake quantity, the resting oxygen intake quantity, the energy coefficients for the heart rate region determined to contain the detected heart rate and a heart rate region lying on a higher heart rate side of the heart rate region determined to contain the detected heart rate, and the heart rate preparation value.

2. The caloric consumption measuring device as recited in claim 1, wherein the second personal data creating component further includes an estimated maximum heart rate calculating section that calculates an estimated maximum heart rate as at least part of the second personal data in accordance with the at least one environmental condition set by the second personal data creating component; and the heart rate preparation value calculating section is configured to calculate the heart rate preparation value using the estimated maximum heart rate and two high and low flex points of the heart rate region determined to contain the detected heart rate.

3. The caloric consumption measuring device as recited in claim 1, further comprising a display component configured to display a caloric consumption calculated by the caloric consumption calculating component.

4. A caloric consumption measuring method configured to measure a caloric consumption of a user during an activity, the method comprising:

inputting at least one personal physical condition of the user;

inputting data indicative of a detected heart rate of the user detected during the activity;

creating first personal data based on the personal physical condition, the creating of the first personal data including calculating a resting oxygen intake quantity as at least part of the first personal data;

inputting at least one environmental condition that is not a physical condition of the user, with whether or not the user exercises regularly, a physical strength of the user, a physical condition of the user, or an experience level of the user with respect to a particular exercise being input as at least part of the environmental condition;

creating second personal data based on the environmental condition, the creating of the second personal data including setting a plurality of flex points as boundary heart rates between a resting metabolism and an active metabolism in accordance with the at least one environmental condition, the flex points being defined by heart rate in relation to oxygen intake quantity, setting a plurality of heart rate regions as at least part of the second personal data in accordance with the at least one environmental condition, and setting energy consumption coefficients as at least part of the second personal data for calculating the energy consumption, being set for each of the heart rate regions and for each case of environmental condition; and calculating caloric consumption based on the detected heart rate and the first and second personal data created, the creating of the second personal data including calculating a maximum oxygen intake quantity as at least part of the second personal data in accordance with the at least one environmental condition, and the calculating of the caloric consumption including determining which of the heart rate regions contains the detected heart rate, calculating a heart rate preparation value for the heart rate region determined to contain the detected heart rate, calculating an oxygen intake quantity at the detected heart rate, and calculating the caloric consumption using the maximum oxygen intake quantity, the resting oxygen intake quantity, the energy coefficients for the heart rate region determined to contain the detected heart rate and for a heart rate region lying on a higher heart rate side of the heart rate region determined to contain the detected heart rate, and the heart rate preparation value.

5. The caloric consumption measuring method as recited in claim 4, wherein the creating of the second personal data further includes calculating an estimated maximum heart rate as at least part of the second personal data in accordance with the at least one environmental condition; and calculating the heart rate preparation value using the estimated maximum heart rate and two high and low flex points of the heart rate region determined to contain the detected heart rate.

* * * * *